United States Patent [19]

Pollard et al.

[11] Patent Number: 5,411,879
[45] Date of Patent: May 2, 1995

[54] FATTY ACYL REDUCTASES

[75] Inventors: Michael R. Pollard, Madison, Wis.; James G. Metz, Woodland, Calif.

[73] Assignee: Calgene Inc., Davis, Calif.

[21] Appl. No.: 149,007

[22] Filed: Nov. 8, 1993

Related U.S. Application Data

[63] Continuation of Ser. No. 659,975, Feb. 22, 1991, abandoned.

[51] Int. Cl.$^6$ .................... C12N 9/02; C12N 9/04; C07K 3/00
[52] U.S. Cl. .................................. 435/190; 435/189; 530/377
[58] Field of Search ................ 435/189, 190; 530/377

[56] References Cited

PUBLICATIONS

L. Hjelmeland et al. Meth. in Enzymology, vol. 104 (1984) pp. 305–319.
A. Khan et al. Arch. of Biochem. & Biophys., vol. 170, (1975) pp. 400–408.
M. Pollard et al. Lipids, vol. 14, #7 (1979) pp. 651–662.
Hjelmeland et al. Methods in Enzymology, vol. 104 (1984) pp. 305–318.
Kolattukudy, P. E., et al., Methods in Enzymology, vol. 71 (1981) pp. 269–272.
Ohlrogge, J. B., et al. Lipids, vol. 13 (1978) pp. 203–210.
Khan, A. A., et al. Archives of Biochem. and Biophysics, vol. 170 (1975) pp. 400–408.
Pollard et al. "Studies on Biosynthesis of Waxes by Developing Jojoba Seed. II. The Demonstration of Wax Biosynthesis by Cell–Free Homogenates," *Lipids* (1979) 14:651–662.
Wu, et al., "Studies of Biosynthesis of Waxes by Developing Jojoba Seed: III. Biosynthesis of Wax Esters from Acyl–CoA and Long Chain Alcohols," *Lipids* (1981) 16:897–702.
Karplus, et al., "Atomic Structure of Ferredoxin–NADP+Reductase: Prototype for a Structurally Novel Flavoenzyme Family," *Science* (1991) 251:60–66.
Wildner and Hallick, "Wax Ester Biosynthesis in *Euglena gracilis*," abstract from *The Southwest Consortium on Plant Genetics and Water Resources Fifth Annual Meeting*, Apr. 22–24, 1990, Las Cruces, N.M.
Pushnik, et al., "Characterization of the Biosynthetic Pathway For Formation of Liquid Wax in Jojoba," abstract from *The Southwest Consortium on Plant Genetics and Water Resources Fourth Annual Meeting*, Feb. 7, 1989, Riverside, Calif.
Kolattukudy, P. E., "Cutin, Suberin, and Waxes", The Biochemistry of Plants, vol. 4 (1980) pp. 571–644.
Yermanos, D. M., "Composition of Jojoba Seed During Development", The Journal of the American Oil Chemistry Society, vol. 52 (1975) pp. 115–117.
Stumpf, P. L., "The Synthesis of Fatty Acids in Plant Systems", Membranes and Transport, vol. 2 (1982) pp. 663–666.
Riendeau, et al., "Enzymatic Reduction of Fatty Acids and Acyl–CoAs to Long Chain Aldehydes and Alcohols", Experientia, vol. 41 (1985) pp. 707–713.
Pollard, et al., "Studies on Biosynthesis of Waxes by Developing Jojoba Seed II. The Demonstration of Wax Biosynthesis By Cell–Free Homogenates", Lipids, vol. 14 No. 7 (1979) pp. 651–660.
Khan, et al., "A Microsomal Fatty Acid Synthetase Coupled to Acyl–CoA Reductase in *Euglena gracilis*", Archives of Biochemistry and Physics, vol. 158 (1973) pp. 411–420.

(List continued on next page.)

*Primary Examiner*—David T. Fox
*Assistant Examiner*—Charles Rories

[57] ABSTRACT

By this invention, a solubilized seed-plant fatty acyl reductase protein is provided, wherein said protein is active in the formation of a fatty alcohol from a fatty acyl substrate. Of special interest is a jojoba embryo reductase protein having a molecular mass of about 32 kD or about 47 kD and sequences obtainable therefrom. Also considered are amino acid and nucleic acid sequences obtainable from such fatty acyl reductases.

9 Claims, No Drawings

PUBLICATIONS

Kolattukudy, et al., "Enzymatic Reduction of Fatty Acids and Alpha-Hydroxy Acids", Methods in Enzymology, Lipids vol. 71: part C (1981) pp. 263–275.

Rodriguez, et al., "Purification of the Acyl Coenzyme A reductase Component from a Complex Responsible for the Reduction of Fatty Acids in Bioluminescent Bacteria", The Journal of Biological Chemistry, vol. 258, No. 8 (1983) pp. 5233–5237.

Wall, et al., "Subunit Structure of the Fatty Acid Reductase Complex from *Phobacterium Phosphoreum*", Biochemistry, vol. 25 (1986) pp. 4315–4321.

Boylan et al., "Lux C, D and E genes of the *Vibrio fischeri* Luminescence Operon Code for the Reductase, Transferase and Synthetase Enzymes Involved in Aldehyde Biosynthesis," Photochemistry and Photobiology, vol. 49, No. 5 (1989) pp. 681–688.

Lloyd, Geoffrey M., "Synthesis and Translocation of Lipids in the Cell Envelope Membranes of *Micrococcus cryophilus*," Microbios, vol. 52 (1987) pp. 29–37.

Bordier, C., "Phase Separation of Integral Membrane Proteins in Triton X-114 Solution." The Journal of Biological Chemistry, vol. 256 No. 4 (1981) pp. 1604–1607.

Morre, et al., "Biological Membranes, A practical Approach." (1987) pp. 37–72.

Hjelmeland, L. M., "Solubilization of Native Membrane Proteins." Method in Enzymology, vol. 182 (1990) pp. 253–263.

Hjelmeland, L. M. "Removal of Detergents from Membrane Proteins.", Methods in Enzymology, vol. 182 (1990) pp. 277–282.

Aebersold, et al., "Internal Amino Acid Sequence Analysis of Proteins Separated by One or Two-Dimensional Gel Electrophoresis After in situ Protease Digestion on Nitrocellulose.", Proceedings of the National academy of Sciences, USA, vol. 84, (1987) pp. 6970–6974.

Goldberg, et al., "Abundance, Diversity and Regulation of mRNA Sequence Sets in Soybean Embryogenesis.", Developmental Biology, vol. 83 (1981) pp. 201–217.

Jaye, et al., "Isolation of Human Anti-Haemophilic Factor IX cDNA Clone Using a Unique 52-Base Acid Sequence of Bovine Factor IX.", Nucleic Acids Research, vol. 11, No. 8 (1983) pp. 2325–2335.

Radke, et al., "Transformation of *Brassica Napus* L. Using *Agrobacterium Tumefaciens*: Developmentally Regulated Expression of a Reintroduced Napin Gene"., Theoretical and Applied Genetics, vol. 75 (1988) pp. 685–694.

Yermanos, D. M., "Quantitative and Qualitative Characteristics of Jojoba Seed.", The Journal of the American Oil Chemistry Society, vol. 53 (1976) pp. 685–694.

Ohlrogge, et al., "Studies on Biosynthesis of Waxes by Developing Jojoba Seed Tissue.", Lipids, vol. 13, No. 3 (1978) pp. 202–210.

Wildner, et al., "Wax Esther Biosynthesis in *Euglena gracilis*.", Abstract from Southwest Consortium on plant Genetics and Water Resources, Las Cruces, N.M., 5th Annual Meeting.

Inui, et al., "Fatty Acid Synthesis in Mitochondria of *Euglena gracilis*.", European Journal of Biochemistry, vol. 142 (1984) pp. 121–126.

FATTY ACYL REDUCTASES

This is a continuation of application Ser. No. 7/659,975, filed Feb. 22, 1991, now abandoned.

TECHNICAL FIELD

The present invention is directed to plant enzymes, methods to solubilize, purify, and obtain such enzymes, amino acid and nucleic acid sequences related thereto, and methods of use for such compositions.

INTRODUCTION

BACKGROUND

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds. As the carbon chain of fatty acyl molecules always contains an even number of carbons, the formula "$C_{2x}$" may also be used to represent carbon chain length.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

Many plants have been studied which store lipid as triacylglycerols composed primarily of long chain (having 16 or 18 carbons) fatty acyl groups. Very long chain (having 20-24 carbons) monounsaturated fatty acyl groups are formed by an acyl-CoA elongation pathway from C18:1 and are found in many plant seeds, notably members of the Crucifereae family. The desert shrub, *Simmondsia chinensis*, better known as jojoba, is unique among higher plants (seed-bearing plants) in its ability to produce and store large amounts of liquid wax as the major component of its seed storage lipid. These simple wax compounds are oxygen esters of very long-chain monoenoic fatty acyl groups and alcohols.

Other types of waxes are formed by some plant species. The synthesis of plant epidermal, or cuticular wax, as well as wax synthesis by bacteria, such as Acinetobacter (Fixter et al. (1986) *J. Gen. Microbiol.* 132:3147-3157) and Micrococcus (Lloyd (1987) *Microbios* 52:29-37), and by the unicellular green algae, Euglena, are well known. However, the composition and biosynthetic pathway of these waxes differs from the jojoba seed wax.

In the formation of Euglena storage wax for instance, it has been demonstrated that the alcohol portion is formed by an NADH-dependent reduction of a fatty acyl compound catalyzed by a fatty acyl-CoA reductase. In jojoba seeds, the reaction is NADPH-dependent. It has been postulated that the reduction of a very long chain fatty acyl-CoA to the corresponding alcohol is dependent upon a single enzyme whose activity has been observed in crude extracts from developing jojoba seeds (Pollard et al. (1979) *Lipids* 14:651-662; Wu et al. (1981) *Lipids* 16:897-902). Also, by comparison, for the formation of plant cuticular waxes, a two step process has been reported (Kolattukudy (1980) in The Biochemistry of Plants (Stumpf, P. K. and Conn, E. E., eds.) Vol.4, p. 571-645). The fatty acyl-CoA is converted to a free aldehyde by the action of an NADH-dependent reductase and the alcohol is subsequently formed by the action of an NADPH-dependent fatty aldehyde reductase.

Further characterization of the enzymes responsible for formation of wax esters in plants has been hindered by the association of these factors with a floating wax pad which is formed upon differential centrifugation of a cell-free homogenate. It is desirable, therefore, for further study of plant fatty acyl reductase proteins to devise a purification protocol whereby these proteins may be separated from the wax pad, especially with a goal to provide a solubilized protein preparation. By establishing these methods, sufficient amounts of plant fatty acyl reductase protein may be obtained, the amino acid sequence of the protein may be determined and/or antibodies specific for the fatty acyl reductase may be obtained. The resulting amino acid sequences may be useful in polymerase chain reaction (PCR) techniques or for screening cDNA or genomic libraries. Alternatively, antibodies may be used for screening expression libraries to identify clones expressing fatty acyl reductase protein. Clones obtained in this manner can be analyzed so that the nucleic acid sequences corresponding to plant fatty acyl reductase are identified.

Relevant Literature

Cell-free homogenates from developing jojoba embryos were reported to have NADPH-dependent fatty acyl-CoA reductase activity. The activity was associated with a floating wax pad which formed upon differential centrifugation (Pollard et al. (1979) supra; Wu et al. (1981) supra).

Conservation of functional residues in known dinucleotide binding folds of several reductase proteins is presented by Karplus et al. (*Science* (1991) 251:60-66).

Solubilization of a multienzyme complex from *Euglena gracilis* having fatty acyl-CoA reductase activity is reported by Wildner and Hallick (Abstract from *The Southwest Consortium Fourth Annual Meeting*, Feb. 7, 1989, Riverside, Calif.).

3000-fold purification of jojoba reductase protein is reported by Pushnik et al. (Abstract from *The Southwest Consortium Fourth Annual Meeting*, Feb. 7, 1989, Riverside, Calif.).

SUMMARY OF THE INVENTION

By this invention, a solubilized fatty acyl reductase protein is provided, wherein said protein is active in the formation of a fatty alcohol from a fatty acyl substrate. The reductase of this invention may be active with a variety of fatty acyl substrates, including acyl-CoAs and acyl-ACPs. The carbon chain length of these substrates may vary, although a given reductase may show preference for a specific chain length acyl substrate or may be active with acyl substrates having a wide range with respect to carbon chain length.

In general, the reductase of this invention has activity towards at least those acyl substrates having a chain length of from 16 to 24 carbons, which carbon chain length may be represented by the formula "$C_{2x}$", where "x" is a number from 8 to 12, although other acyl substrates may be tested and further activities discovered. In addition, having obtained the reductase protein of this invention, further manipulations are now possible as described in further detail below. These manipulations may lead to production or discovery of other related reductases.

Thus, in a first aspect, this invention relates to solubilized protein preparations demonstrating fatty acyl reductase enzymatic activity, and is exemplified by a seed-plant protein preparation. Such a preparation is produced by fractionation of jojoba embryos to produce a microsomal membrane preparation and solubilization of the reductase protein from this membrane preparation. The jojoba reductase is shown to prefer very long chain acyl-CoA substrates, although activity with other acyl substrates is also observed, and is confirmed to be NADPH-dependent.

Further, proteins are identified whose staining intensities correlate with acyl reductase activity, and the molecular masses of these proteins are determined to be about 47 kD and 32 kD. In addition, the 47 kD protein associated with reductase activity is shown to have the following N-terminal amino acid sequence (SEQ ID NO: 1):

Xaa Xaa Ala Ala Thr Ile Leu Ala Gly Val Xaa Val Leu Val Ala Leu
1           5                   10                  15

Tyr Asp Gly Leu.
20

Methods of obtaining an acyl reductase protein through purification from seed-plant sources are thus provided, as well as methods to obtain amino acid sequences of these reductase proteins.

In a different aspect of this invention, nucleic acid sequences associated with a reductase of this invention are considered. Methods are described whereby these sequences may be identified and obtained from the amino acid sequences of the reductase proteins of this invention. Uses of the structural gene sequences for isolation of other reductase sequences, as well as in recombinant constructs for transcription of reductase nucleic acid sequences and/or expression of reductase proteins in host cells are described. Uses of other nucleic acid sequences associated with reductase protein are also considered, such as the use of 5' and 3' noncoding regions.

In yet a different aspect of this invention, cells containing the recombinant constructs of this invention are considered. In particular, cells containing preferred substrates of the jojoba reductase, such as those in embryos of Brassica plants are considered.

In addition, cells containing the reductase protein of this invention as the result of expression from the recombinant constructs of this invention are considered, and a method of producing a reductase in a host cell is provided. Accordingly, a reductase protein that is recovered as the result of expression of that protein in a host cell is also considered in this invention. Further, it may be recognized that the reductases of this invention may find application in the production of fatty alcohols in such host cells.

DETAILED DESCRIPTION OF THE INVENTION

A fatty acyl reductase of this invention includes any sequence of amino acids, such as protein, polypeptide or peptide fragment, which is active in catalyzing the reduction of a fatty acyl group to the corresponding alcohol. By fatty acyl group is intended any fatty acyl group, either free or covalently bound to a carrier, such as ACP or coenzyme A.

Other enzymes may or may not be required for the reduction of the fatty acyl group to the alcohol, as this enzymatic reaction requires two reduction steps. In the first step, the acyl group is converted to an aldehyde, which is then reduced to the corresponding alcohol. Thus, the reductase of this invention may be active through two reduction steps, from acyl to alcohol, or may catalyze the reduction to the aldehyde, which is then further reduced to the alcohol by a second enzyme. The fatty acyl reductase of this invention is also referred to hereafter as "acyl reductase" or "reductase".

Thus, this invention relates to seed-plant fatty acyl reductases which convert fatty acyl groups to alcohols. More particularly, this invention relates to those NADPH-dependent reductases. In addition, it is noted that a plant fatty acyl reductase of this invention may have activity towards both fatty acyl-CoA or fatty acyl-ACP molecules. The activity observed may depend upon the substrate available. However, preferential activity toward very long chain acyl-CoA substrates is desired for manipulation of the FAS acyl-CoA elongation pathway.

By this invention, it has been determined that the seed-plant fatty acyl reductase protein is an integral membrane protein. In general, membrane associated proteins are difficult to purify as they tend to lose enzymatic activity when they are solubilized, i.e. separated from the membrane environment in which they normally function. However, obtaining a solubilized seed-plant fatty acyl reductase which still retains its enzymatic activity can permit various uses which are not possible with a membrane-bound protein.

For example, once a purified or partially purified acyl reductase protein is obtained, it may be immobilized and used in a reactor system to prepare fatty alcohols in the presence of a reduced pyridine nucleotide regenerating system. Further, study of the reductase protein may lead to site-specific mutagenesis studies to further characterize and improve its catalytic properties or to alter its acyl substrate specificity. A reductase with altered substrate specificity may find application in conjunction with other FAS enzymes. For example, a medium chain (C12-C14) preferring plant thioesterase (see copending U.S. patent application Ser. No. 07/620,426), and an appropriate acyl transferase may be used in conjunction with an altered reductase to produce medium-chain alcohols, which may then be esterified to fatty acids to yield esters.

One significant factor to be considered when working with membrane bound proteins is the extent of the association of the protein with the membrane. Both peripheral and integral membrane proteins are known. Peripheral proteins are typically hydrophilic in nature, only loosely associated with the membranes and easily solubilized. Integral proteins, on the contrary, have highly hydrophobic regions embedded in the lipid membrane and often must be associated with lipids if they are to retain enzymatic activity.

Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized protein preparation of this invention, a microsomal membrane preparation of seed-plant tissue which comprises acyl reductase activity is desired. Standard microsomal membrane preparations utilize a $100,000 \times g$ sucrose density gradient centrifugation of a cell-free homogenate which yields a pellet, a supernatant, and in some instances (especially with fractionation of oilseeds), a floating fat pad. Generally, the membranes are recovered in the pellet and are free of whole cells, nuclei and soluble protein.

With jojoba embryo cell-free homogenates, however, following sucrose density gradient centrifugation, the largest fraction of the desired acyl reductase activity is found in a floating waxy fat pad. By this invention, therefore, methods have been devised by which the membrane fraction containing active acyl reductase protein is obtained free of the floating fat pad. A critical step in this process is the removal of the seed coat from the jojoba embryos as the coats are found to contain a factor(s) that interferes with enzymological measurements. Also, high salt solution is found to be important in this process, the steps of which are described below and in more detail in the examples which follow.

A powder is produced from a jojoba embryo sample, and a homogenate is prepared by homogenizing the powder in a high salt (3M NaCl) sucrose (0.3M) solution at a ratio of 80 ml of solution per 20 gm embryos. The homogenate is then filtered and centrifuged at $100,000 \times g$ for approximately one hour, wherein a pellet, supernatant and fat pad are obtained. The fat pad is removed and the supernatant is collected and dialyzed against a 1M NaCl solution which also contains 100 mM HEPES (pH 7.5), 2 mM DTT and 0.5 mM EDTA. The dialyzate is then centrifuged at $100,000 \times g$ for approximately one hour, wherein a pellet, DP2, is obtained which comprises microsomal membranes having acyl-CoA reductase activity.

Further characterization of the acyl reductase activity of a candidate reductase in the microsomal membrane preparation may be facilitated by developing an optimized specific assay for acyl reductase. For example, with jojoba an assay is employed which utilizes very long chain acyl-CoA molecules as substrates and which is conducted under high salt conditions, high salt having been found to significantly increase the detectable acyl-CoA reductase activity. This assay is described in detail in Example 1.

Another critical stage for further enzyme characterization and purification is that of obtaining solubilized reductase protein that is separated from its native lipid bilayer membrane environment, but retains substantial amounts of measurable reductase enzymatic activity. The removal of integral membrane proteins from the lipid bilayer is typically accomplished using amphiphilic detergents in aqueous solution, although organic solvents have also been used in a few cases. Many different detergents are available, both ionic and nonionic, which vary in their dissociating effects, critical micelle concentration (CMC), effect on enzymatic activity and further purification, and ease of removability from the solution. Many different detergents and methods of solubilization of membrane proteins are known to those skilled in the art, and are also reviewed by Neugebauer (*Methods Enzymol.* (1990) 182:239–253) and Hjelmiland (*Methods Enzymol.* (1990) 182:253–264).

Often, detergents which are used to solubilize membrane proteins are found to inhibit the enzymatic activity of a desired protein. Several detergents were tested for solubilization of jojoba acyl reductase, representing a wide range of characteristics, and all were found to be inhibitory. However, as apparent detergent inhibition of reductase activity may be due to some effect other than irreversible inhibition of the enzyme, the reversibility of inhibition by CHAPS was examined.

Although strong inhibition by the detergent CHAPS (3-[(3-cholamidopropyl)-dimethyl-ammonio]-1-propanesulfonate) at concentrations above the CMC was seen, it was found that if the enzyme was exposed to CHAPS on ice, and then returned to a CHAPS concentration at or below the CMC value, complete recovery of reductase activity was obtained. Thus, reductase is not irreversibly inhibited by the detergent CHAPS. A protocol for solubilizing jojoba acyl reductase activity utilizing the detergent CHAPS has been devised which yields approximately 85% of the reductase activity from the microsomal membrane preparation. This method is discussed in detail in Example 2. Similarly, studies of reversibility of apparent reductase inhibition by other detergents may be conducted to identify other useful detergents for solubilization of acyl reductase activity for jojoba or other candidate reductases.

Having obtained the solubilized acyl reductase protein, it can be seen that further experiments to characterize the enzyme as to substrate specificity, cofactor requirements and possible activity inhibiting agents may now be conducted. For example, it has been found that the jojoba acyl reductase of this invention has a broad range of substrates, including ACP and CoA substrates. For example, activity towards acyl-ACP substrates having at least 16 carbons is observed, as well as activity towards acyl-CoA substrates having at least 18 carbons. A preferred activity toward tetracosenayl-CoA (C24:1) is observed.

Protein preparations may be further enriched for a candidate plant acyl reductase protein, for example by chromatography over an immobilized reactive dye. Many such reactive dye matrices are known, including the Cibacron Blue F3GA (Blue A) used in this invention. By this invention it is demonstrated that jojoba acyl reductase activity binds to such a column when loaded in a buffer containing approximately 0.2M NaCl, while greater than approximately 85% of other protein passes through or is removed in subsequent washes. Further, it is demonstrated that jojoba acyl activity can be recovered by elution from the Blue A column in a buffer containing approximately 1.5M NaCl.

Fractions of the candidate reductase protein preparation in which the acyl reductase activity is further purified may also be obtained by applying the enriched protein preparation from the Blue A column to a column packed with a size exclusion matrix. In particular, a narrow range sizing column matrix, such as Ultragel AcA54 or Sephacryl S100, is useful in obtaining further purified jojoba acyl reductase fractions. Of special interest are methods and buffers which may be utilized to obtain recovery, in one main peak, of greater than approximately 40% of the reductase activity that is loaded to such a column or its equivalent. Further, it is discovered by calibrating this column using known protein standards that the apparent molecular mass of a jojoba protein having reductase activity is approximately 49 kD.

In addition, the fractions comprising acyl reductase activity of this invention may be concentrated and subjected to further techniques, such as SDS polyacrylamide gel electrophoresis and subsequent staining. In this manner, protein bands on the gels can be identified whose staining intensity correspond to levels of acyl reductase activity in these fractions. Among the bands so identified of a jojoba reductase protein preparation is a band representing a protein of approximately 47 kD molecular mass and a less prominent band of approximately 32 kD molecular mass.

Either the 47 kD or the 32 kD protein bands may correspond to the apparent molecular mass of the jojoba acyl reductase as identified by the size exclusion chromatography discussed above. The size exclusion column is run under non-denaturing conditions, while the SDS PAGE analysis is conducted on denatured protein. As reductase activity could rely on a combination of two or more subunits, the size of protein bands which correlate with reductase activity on denaturing gels could be considerably less than the estimated 49 kD molecular mass of the active jojoba acyl reductase if the reductase is comprised of two or more subunits. Further, the estimate of molecular mass from size exclusion chromatography may be inaccurate by as much as 40%. Thus, by this invention protein bands are identified from partially purified jojoba embryo extracts whose staining intensities correlate with acyl reductase activity.

Further purification techniques can be utilized to provide additional separation of these protein bands. For example, affinity chromatography using a substance that will bind to the acyl reductase, such as an acyl-CoA or acyl-ACP molecule, may prove useful in further purification techniques. For example, as described in Example 2, palmitoyl-ACP has been shown to bind to jojoba acyl reductase and thus may find use in further purification. Also, tests indicate that the jojoba acyl reductase of this invention has an essential sulphydryl group. Thus, sulphydryl blocking reagents, such as Ellman's reagent, may also be useful for further column purification. By using further purification techniques, or by preparation of antibodies, or alternatively by obtaining amino acid sequence of the candidate proteins, a substantially pure acyl reductase may be obtained.

Proteins associated with acyl reductase activity can be recovered as substantially purified protein preparations and the amino acid sequence of a candidate acyl reductase protein can be obtained. Recovery of substantially purified protein can be accomplished using a variety of methods. For example, polyacrylamide gels may be run and the proteins transferred to a membrane support, such as nitrocellulose or polyvinylidenedifluoride (PVDF). The sections of these membranes which contain the identified proteins may then be obtained such that the identified proteins are substantially free of other proteins. Using techniques known in the art and also described in the following examples, the proteins may be removed from the membranes and further manipulated such that their amino acid sequences are determined.

For example, amino acid sequence can be determined by sequencing N-terminal amino acid regions from whole protein or by preparing fragments of the desired protein by digestion with the chemical cyanogen bromide, or alternatively by enzymatic cleavage using proteases. Examples of proteases which may be useful include endoproteinase lysC, gluC, AspN and trypsin. The fragments obtained in this manner may then be purified and sequenced in accordance with methods familiar to those skilled in the art.

It has been found that the 47 kD jojoba protein which correlates with acyl reductase activity has the N-terminal amino acid sequence (SEQ ID NO: 1):

Xaa Xaa Ala Ala Thr Ile Leu Ala Gly Val Xaa Val Leu Val Ala Leu
1             5                  10                 15

Tyr Asp Gly Leu
     20 wherein the three-letter abbreviation for amino acids is used; Xaa indicates unidentified amino acids. The unidentified amino acid at position 11 is likely a leucine.

An amino acid sequence of a cyanogen bromide fragment of the 47 kD protein is similarly obtainable as further described in Example 4. The sequence (SEQ ID NO: 2) of this fragment is determined as:

Ile Xaa Val Gln Gly Pro Glu Xaa Ile Ala Phe Asp Leu Xaa Xaa
1             5                  10                 15 wherein the three-letter abbreviation for amino acids is used and Xaa indicates an unidentified amino acid. It is postulated that the unidentified amino acid at position 2 may be either serine or glutamine, at position 8 it may be serine, at position 14 it may be leucine, and that at position 15 it may be glycine. In a similar manner, additional amino acid sequences of the jojoba 47 kD and 32 kD proteins whose staining intensities correlate with acyl reductase activity can be determined.

Further experiments to confirm the identity of a candidate reductase may also be desirable, such as expression of the protein in *E. coli* and subsequent verification of reductase activity in a cell extract. Other testing may include immunological assays, whereby antibodies specific for the candidate protein are prepared and found to inhibit reductase activity in protein preparations.

Moreover, it is desirable to isolate nucleic acid sequences from amino acid sequences determined for the proteins associated with acyl reductase activity, both to confirm the identity of an acyl reductase protein and to provide for transcription of the sequences and/or expression of the protein in host cells, either prokaryotic or eukaryotic. Various manipulations may be necessary for expression of the reductase in cells. For example, the protein if produced at a high level in a prokaryote, such as *E. coli*, may be disruptive or even toxic due to insertion into cell membranes. Low level expression using a weak promoter, thus may be desirable. Alternatively, if a leader peptide is discovered which may be responsible for membrane insertion, constructs may be prepared which contain only those nucleic acid sequences that encode a mature reductase protein. In this manner the reductase protein may be produced in *E. coli* cells. Although activity may not be detected, since the protein likely would not be inserted into the membrane bilayer, the presence of the reductase protein in *E. coli* cells may be confirmed by other means, such as using antibody preparations.

As the acyl reductase is a membrane bound protein, it may be desirable to express a candidate protein in a plant cell in order to verify the activity. Electroporation or bombardment of plant tissue for transient expression may be useful for this purpose. Ultimately, stable plant expression in a plant, such as a member of the Brassica genus, which produces substrates recognized by this enzyme will be useful. In this manner, the acyl alcohol products, which have uses in pharmaceuticals, cosmetics, detergents, plastics, and lube oils may be obtained.

The nucleic acids of this invention may be genomic or cDNA and may be isolated from cDNA or genomic libraries or directly from isolated plant DNA. Methods of isolation of gene sequences once a protein is isolated and/or amino acid sequence of the protein is obtained are known to those skilled in the art.

For example, antibodies may be raised to the isolated protein and used to screen expression libraries, thus identifying clones which are producing the plant acyl reductase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

Acyl reductase nucleic acid sequences of this invention include those corresponding to the jojoba acyl-CoA reductase protein, as well as sequences obtainable from the jojoba protein or nucleic acid sequences. By "corresponding" is meant nucleic acid sequences, either DNA or RNA, including those which encode jojoba acyl reductase protein or a portion thereof, regulatory sequences found 5' or 3' to said encoding sequences which direct the transcription or transcription and translation (expression) of the reductase in jojoba embryos, intron sequences not present in the cDNA, as well as sequences encoding any leader or signal peptide of a precursor reductase protein that may be required for insertion into the endoplasmic reticulum membrane, but is not found in the mature, or processed, acyl reductase enzyme.

By sequences "obtainable" from the jojoba sequence or protein, is intended any nucleic acid sequences associated with a desired fatty acid reductase protein that may be synthesized from the jojoba acyl reductase amino acid sequence, or alternatively identified in a different organism, and isolated using jojoba reductase nucleic acid sequences or antibodies prepared against the jojoba reductase protein as probes. In this manner, it can be seen that sequences of other acyl reductases that are isolated from a desired organism using the jojoba sequences, either by nucleic acid hybridization or antigenic methods, may similarly be used to isolate still other acyl reductases. Such reductases which are derived through seed-plant reductases isolated via jojoba reductase are likewise considered "obtainable" herein.

For isolation of nucleic acid sequences, cDNA or genomic libraries may be prepared using plasmid or vital vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual*, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding acyl reductase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding an acyl reductase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba acyl reductase can be prepared by injecting rabbits or mice (or other appropriate small mammals) with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba reductase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (*Focus* (1989) BRL/Life Technologies, Inc. 11:1–5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques, for example as provided in Maniatis, et al. (supra). In this manner, it is verified that the clones encode a related acyl reductase protein. Other seed-plant fatty acyl reductases may be obtained through the use of the "new" reductase in the same manner as the jojoba reductase was used.

It will be recognized by one of ordinary skill in the art that acyl reductase nucleic acid sequences of this invention may be modified using standard techniques of site specific mutation or PCR, or modification of the sequence may be accomplished in producing a synthetic nucleic acid sequence. These modified sequences are also considered acyl reductase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an acyl reductase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the reductase protein) may be synthesized using codons preferred by a selected host. Host-preferred codons may be determined, for example, from the codons used most frequently in the proteins expressed in a desired host species.

The nucleic acid sequences associated with acyl reductase proteins will find many uses. For example, recombinant constructs can be prepared which can be used as probes or will provide for expression of the acyl reductase protein in host cells. Depending upon the intended use, the constructs may contain the sequence which encodes the entire reductase, or a portion thereof. For example, critical regions of the reductase, such as an active site may be identified. Further constructs containing only a portion of the reductase sequence which encodes the amino acids necessary for a desired reductase activity may thus be prepared.

Expression in host cells which contain preferred substrates of the acyl reductase protein, may allow for production of fatty acyl alcohols from the corresponding fatty acyl substrates. Useful systems for expression of the reductase protein include prokaryotic cells, such as *E. coli*, yeast cells, and plant cells, both vascular and nonvascular plant cells being desired hosts. In this manner, the reductase protein may be produced. In addition, site-specific mutagenesis of encoding sequences may be used to study the effects of specific mutations on reactive properties of the reductase protein.

Additionally, antisense constructs may be prepared which provide for transcription of an antisense copy of an acyl reductase encoding sequence or fragment thereof. In this manner, the amount of the reductase protein produced in a target host organism may be reduced.

The DNA sequence encoding an acyl reductase of this invention may be combined with foreign DNA sequences in a variety of ways. By "foreign" DNA sequences is meant any DNA sequence which is not naturally found joined to the reductase, including combinations of DNA sequences from the same organism which are not naturally found joined together. For example, it may be desirable to join sequences encoding a transit peptide to reductase sequences of this invention. In this manner, the reductase may be targeted to a chloroplast where fatty acyl substrates, particularly fatty acyl-ACPs are available.

The DNA sequence encoding an acyl reductase of this invention may be employed in conjunction with all or part of the gene sequences normally associated with the reductase. In its component parts, a DNA sequence encoding reductase is combined in a recombinant construct having, in the 5' to 3' direction of transcription, a transcription initiation control region capable of promoting transcription and translation in a host cell, the nucleic acid sequence encoding reductase and a transcription termination region.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the recombinant constructs will involve regulatory regions functional in plants which provide for production of acyl reductase. The open reading frame, coding for the plant reductase or functional fragment thereof will be joined at its 5' end to a transcription initiation regulatory region such as the wild-type sequence naturally found 5' upstream to the reductase structural gene. Numerous other promoter regions are available which provide for a wide variety of constitutive or regulatable, e.g., inducible, expression of the structural gene functions.

Among sequences known to be useful in providing for constitutive gene expression are regulatory regions associated with Agrobacterium genes, such as for hopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the acyl reductase protein is desired in a plant host, the use of all or part of the complete plant acyl reductase gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto", all of which copending application are incorporated herein by reference. Transcription initiation regions which are preferentially expressed in seed tissue, i.e., which are undetectable in other plant parts, are considered desirable for fatty alcohol production in order to minimize any disruptive or adverse effects of the gene product in other plant parts.

Regulatory transcription termination regions may be provided in recombinant constructs of this invention as well. Transcription termination regions may be provided by the DNA sequence encoding the plant acyl reductase or a convenient transcription termination region derived from a different gene source, especially the transcription termination region which is naturally associated with the transcription initiation region. The transcript termination region will contain at least about 0.5 kb, preferably about 1-3 kb of sequence 3' to the structural gene from which the termination region is derived.

Plant expression constructs having a plant acyl reductase as the DNA sequence of interest for expression thereof may be employed with a wide variety of plant life, particularly, plant life which produce very long chain fatty acyl-CoA molecules, such as Brassica, and in particular high erucic acid varieties of rapeseed. Other plants of interest produce desirable substrates, such as medium or long chain fatty acyl molecules, and include but are not limited to rapeseed (Canola varieties), sunflower, safflower, cotton, Cuphea, soybean, peanut, coconut and oil palms, and corn. Depending on the method for introducing the DNA expression constructs into the host cell, other DNA sequences may be required. Importantly, this invention is applicable to dicotyledyons and monocotyledons species alike and will be readily applicable to new and/or improved transformation and regeneration techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

In developing the recombinant construct, the various components of the construct or fragments thereof will normally be inserted into a convenient cloning vector which is capable of replication in a bacterial host, e.g., E. coli. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

When Agrobacterium is utilized for plant transformation, it may be desirable to have the desired nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ricontaining the T-DNA for recombination may be armed (capable of causing gall formation), or disarmed (incapable of causing gall formation), the latter being permissible so long as a functional complement of the vir genes, which encode trans-acting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region(s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells.

For transformation of Brassica cells, Agrobacterium transformation methods may be used. One such method is described, for example, by Radke et al. (*Theor. Appl. Genet.* (1988) 75:685–694).

The invention now being generally described, it will be more readily understood by reference to the following examples, which are included for purposes of illustration only and are not intended to limit the invention unless so stated.

EXAMPLES

Example 1

Acyl-CoA Reductase Assays

Methods to assay for acyl-CoA reductase activity in microsomal membrane preparations or solubilized protein preparations are described.

A. Radiolabeled Material

Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$_{14}$C]cyanide with the corresponding alkyl mesylate, followed by the base hydrolysis of the alkyl nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10Ci/mole. Other [1-$^{14}$C] acyl-CoAs, such as [1-$^{14}$C]tetracasenoyl-CoA, were purchased from Amersham (Arlington Heights, Ill.). [1-$^{14}$C]hexadecanal is prepared by the dichromate oxidation of [1-$^{14}$C]hexadecan-1-ol, according to a microscale modification of the method of Pletcher and Tate (*Tet. Lett.* (1978) 1601–1602). The product is purified by preparative silica TLC, and stored as a hexane solution at −70° C. until use.

B. Assay for Reductase Activity in a Microsomal Membrane Preparation

Reductase activity in a microsomal membrane preparation is measured by incubation of 20 μM [1-$^{14}$C]acyl-CoA (usually tetracosenoyl-CoA, sp. act. 2–5 Ci/mol) with the sample to be assayed and 2 mM NADPH, in a total volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as refered to hereafter is added from a 1M stock solution adjusted to pH 7.5).

The assay is started by the addition of acyl-CoA substrate and the incubation is carried out at 30° C. for one hour. The assay is terminated by placing the assay tube on ice and immediately adding 0.25 ml isopropanol:acetic acid (5:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Six ml of hexane/isopropanol (3:2, v/v) is added to the terminated assay. The sample is vortexed, 2 ml of aqueous sodium sulphate solution (5.5% w/v) is added, and the sample is again vortexed.

C. Assay for Solubilized Reductase Activity

For assaying solubilized reductase activity, several changes, including the addition of salt for enzyme activation, are required. The assay buffer for a solubilized reductase assay is as indicated above for the microsomal membrane preparation assay, with the following changes:

a. NaCl is added to a final concentration of between 0.3 and 0.5M, b. EDTA is included at ~1 mM, and c. the enzyme sample to be assayed, which typically contains 0.75% CHAPS, is diluted to ≦0.3% (the CMC for CHAPS is ~0.5%).

D. Analysis of Assay Products

For analyzing the products of either the microsomal membrane preparation reductase assay or the solubilized reductase assay, two protocols have been developed. One protocol, described below as "extensive assay" is more time-consuming, but yields more highly quantitative results. The other protocol, described below as "quick assay" also provides a measure of reductase activity, but is faster, more convenient, and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of heptane, and an aliquot is assayed for radioactivity by liquid scintillation counting. The remainder of the sample can be used either for TLC analysis of the labeled classes, or for derivatization to cleave the wax esters, and thereby give a measure of total alcohol produced.

For lipid class analysis the sample is applied to a silica TLC plate, and the plate is developed in hexane/diethyl ether/acetic acid (80:20:1 v/v/v). The distribution of radioactivity between the lipid classes, largely wax esters (when ligase is present, as in the microsomal membrane preparation assay), free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis.

For cleavage of the wax esters, a scaled down protocol based on the Grignard derivatization protocol of Pina et al. (*Lipids* (1987) 22:358–361) is used. The sample, plus 200 μg of carrier wax esters, is dried down in a glass tube fitted with a teflon-lined screw cap. Dry diethyl ether (0.4 ml), ethyl acetate (3 μl), and 3M ethyl magnesium bromide in diethyl ether (0.1 ml) are added sequentially. The sample is vortexed and allowed to stand at room temperature for at least 2 hours, after which water-saturated diethyl ether is carefully added to destroy excess reagent. Two ml each of 1M HCl and hexane are added and the tube is vortexed. The upper organic phase is washed with water (2×2 ml) and evaporated to dryness in the presence of 50–100 μl of ethanol.

The sample is resuspended in 50–100 μl of hexane and applied to a TLC plate. Both normal and reversed-phase TLC systems have been used for the analysis. Normal phase TLC uses a silica TLC plate, developed with hexane/diethyl ether/acetic acid (70:30:2 v/v/v). The reversed phase system uses C18 plates developed in methanol.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in heptane and spotted on TLC plates and developed and scanned as described for the detailed assay. In this manner the percentage of the total counts which are incorporated into alcohol is determined.

Example 2

Characterization of Jojoba Acyl-CoA Reductase

Methods to obtain jojoba protein preparations having reductase activity and results of studies of this enzymatic activity are presented.

A. Seed Development and Acyl-CoA Reductase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Acyl-CoA reductase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for acyl-CoA reductase activities as measured in either a cell free homogenate or a membrane fraction, indicate a large induction in reductase activity which peaks at approximately 115 days after anthesis. Embryos for enzymology studies were thus harvested between about 90 to 110 days postanthesis, a period when the reductase activity is high, lipid deposition has not reached maximum levels, and the seed coat is easily removed. The highest rate of increase of reductase activity is seen between days 80 and 90 postanthesis. Embryos for cDNA library construction were thus harvested between about 80 to 90 postantanthesis when presumably the rate of synthase of reductase protein would be maximal. Correspondingly, the level of mRNA encoding acyl-CoA reductase would be presumed to be maximal at this stage.

B. Fractionation Studies

Early attempts to fractionate jojoba embryo samples resulted in variable distribution of reductase activity in the fat pad, supernatant and particulate fractions resulting from centrifugation. A large number of treatments to potentially affect the distribution of activity were tested, such as sonication, floatation gradients, and the addition of various agents to the extraction buffer. The inclusion of salts in the extraction buffer resulted in the greatest improvement in recovery of ligase activity in the supernatant fraction upon centrifugation at 100,000×g for one hour. The extraction buffer consists of 3M NaCl, 0.3M sucrose, 100 mM HEPES, 2 mM DTT, and the protease inhibitors, 1 mM EDTA, 0.7 μg/ml leupeptin, 0.5 μg/ml pepstatin and 17 μg/ml phenylmethanesulfonyl fluoride (PMSF).

C. Microsomal Membrane Preparations

Particles having high levels of reductase activity can be obtained from the supernatant fraction described above either by dialysis followed by centrifugation at 100,000×g or by ammonium sulphate fractionation. The dialysis method is described in detail in Example 3. Further analysis of these particles having reductase activity such as density gradient centrifugation, gel permeation chromatography, and protein/phospholipid analysis establishes that these particles represent a membrane fraction. This membrane preparation also has high cytochrome C reductase activity, which activity is used as a marker for endoplasmic reticulum (ER) membranes. These studies thus establish that the reductase protein is associated with membranes.

For ammonium sulphate fractionation, the 100,000×g supernatant is obtained from jojoba embryos essentially as described in Example 3. An equal volume of ammonium sulphate solution (33.2 g/100 ml) is slowly added to the supernatant fraction (with stirring) to bring the ammonium sulphate concentration to 30%, a concentration that will effectively precipitate the reductase enzyme. Following 30 additional min. of stirring, the suspension is centrifuged at 26,000×g for 30 min., and the pellet resuspended in one tenth of the volume of the first supernatant fraction, S1, using a solution consisting of 25mm HEPES, 1M NaCl, 1 mM DTT, 0.1 mM PMSF. The suspension is centrifuged at 100,000×g for one hour, and the resulting pellet resuspended in 25 mM HEPES, 10% glycerol (again at 1/10th of the S1 volume). Centrifugation of this suspension at 100,000×g yields the washed microsomal pellet, P4, which is resuspended in 1/20th of the S1 volume of 25 mM HEPES, 10% glycerol yielding a protein fconcentration of about 3–4 mg/ml. Aliquots are frozen at −70° C. for later use.

D. Study of Membrane Association of Reductase Activity

The Triton X114 phase fractionation procedure described by Bordier (*J. Biol. Chem.* (1981) 256:1604–1607) is used to determine whether the jojoba reductase is an integral membrane protein, or is more loosely associated with the membrane layer (more highly hydrophillic proteins). This technique essentially involves incubation of the membranes with 1% Triton X114 on ice followed by raising the temperature of the mixture above the cloud point of the detergent under these conditions (the cloud point is the temperature at which very large micelles begin to spontaneously form, for 1% Triton X114 this is ~20° C. ). Upon centrifugation, two distinct phases can be observed, a lower detergent rich phase and an upper detergent depleted phase (refered to here as the aqueous phase). Integral membrane proteins have been shown to preferentially partition into the detergent rich phase while more highly hydrophilic proteins are recovered in the aqueous phase. When jojoba membrane preparations are subjected to this Triton X114 phase fractionation protocol, reductase activity is associated with the detergent enriched phase and no reductase activity is detected in the aqueous phase. This is evidence that the reductase enzyme is an integral membrane protein.

E. Further Characterization of Reductase Enzyme

The microsomal membrane preparation described above is used for further characterization of the reductase enzyme. The reductase enzyme was shown to be active over the range of pH 5–9. Characterization experiments were conducted at pH 7.5, which is close to the presumed physiological pH of the cytoplasm.

1. Salt Effects: A variety of salts were examined for their effect on reductase activity using a standard concentration of 0.5M for monobasic salts. Salts with divalent cations or anions were examined at 0.167M (to give the same ionic strength as the 0.5M monobasic salts) and also at 0.5M. Up to 15-fold stimulation is observed with the addition of 0.5M NaCl. Other salts, both monovalent and divalent (such as LiCl, KCl, $MgCl_2$, $CaCl_2$, and $Na_2SO_4$) were also shown to stimulate reductase activity, although generally to a lesser degree as compared to the NaCl stimulation. Strongly chaotropic salts, KSCN and NaSCN gave no stimulation or marginal stimulation of reductase activity.

2. Other Effectors: Dithiothreitol (DTT) was found to be stimulatory to reductase activity, but not obligatory, while ethylenediaminetetraacetic acid (EDTA) gave some stimulation, with the optimum concentration being 2.5 mM. A small stimulation of activity was observed at low (0.02–0.075 mg/ml) BSA (bovine serum albumin) concentrations, while inhibition of activity was observed at BSA concentrations at and above 0.2 mg/ml.

Earlier observations that the acyl-CoA reductase is an NADPH specific activity (Pollard et al., supra) were confirmed. No NADH-dependent activity was measurable above background (<2% of the NADPH-dependent activity). Also, both water-soluble end-products of the reductase reaction, CoA and NADP+, give significant inhibition of activity (at millimolar concentrations), while NADH and NAD+ have marginal effects on activity.

3. Substrate Specificity: The thioesters of various chain length fatty acids, acyl-ACPs and acyl-CoAs, were compared as substrates for the reductase enzyme. Tests were conducted at substrate concentrations of 10 uM, as the tetracosenoyl-CoA (24:1-CoA) substrate shows strong substrate inhibition at greater concentrations. NaCl concentration in these assays is 0.5M. Results of the substrate specificity experiment are presented in Table 3 below.

TABLE 3

Acyl Specificity of the Reductase

| Acyl Group | Reductase Activity (pmoles/min/μl) | |
| --- | --- | --- |
| | Acyl-ACP (10 μM) | Acyl-CoA (10 μM) |
| 12:0 | <0.01 | <0.15 |
| 16:0 | 2.9 | <0.4 |
| 18:0 | — | 1.4 |
| 18:1 | 1.05 | 0.75 |
| 20:1 | — | 1.0 |
| 22:1 | — | 1.0 |
| 24:1 | — | 19.9 |

Tetracosenoyl-CoA has the highest substrate activity of those tested, and is thus used for reductase assays in further enzyme purification and characterization experiments. Of interest, palmitoyl-CoA (C16:0-CoA) and palmitoyl-ACP (C16:0-ACP) were directly compared as substrates. The activity towards palmitoyl-CoA was barely above background, while activity towards palmitoyl-ACP was high. Previously, stearoyl-ACP (C18:0-ACP) was shown to have activity as a substrate (Pollard et al., supra).

Also of interest, although palmitoyl-CoA appears to be a poor substrate for the reductase enzyme, in a competitive inhibition experiment conducted using unlabelled palmitoyl-CoA (0–30 μM) and [1-14C]tetracosenoyl-CoA (20 μM), 50% inhibition of reductase activity towards tetracosenoyl-CoA occurred at 5 μM palmitoyl-CoA. Thus, although palmitoyl-CoA is a poor substrate under the assay conditions, it is an effective inhibitor.

4. Reductase Inhibitor Assays: Several known inhibitors of other types of reductase proteins were tested for their effect on the jojoba acyl-CoA reductase activity. Mevinolin, which is a strong inhibitor of HMG-CoA reductase (3-hydroxyl-3-methylglutaryl-coenzymeA reductase), only had an effect at relatively high concentrations (100uM) compared to the concentrations inhibitory to HMG-CoA reductase (Ki of approximately 1 nM). Cerulinen is well known to covalently bind to β-ketoacyl thioester synthases, but has no strong inhibitory effect on the jojoba acyl-CoA reductase.

Sulphydryl blocking agents were also screened for their effect on reductase activity. N-ethylmaleimide was shown to strongly inhibit activity, while para-hydroxymercuribenzoate also had some inhibitory effect, and iodoacetamide had no effect. This evidence leads to the conclusion that the acyl-CoA reductase has an essential sulphydryl group that shows considerable selectivity towards various sulphydryl blocking reagents.

Example 3

Purification of Acyl-CoA Reductase

Methods are described which may be used for isolation of a jojoba membrane preparation having reductase activity, solubilization of reductase activity and further purification of the reductase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 20 g of embryos are processed.

The powder is added, at a ratio of 80 ml of solution per 20 g of embryos, to the following high salt solution: 3M NaCl, 0.3M sucrose, 100 mM HEPES, 2 mM DTT, and the protease inhibitors, 1 mM EDTA, 0.7 μg/ml leupeptin, 0.5 μg/ml pepstatin and 17 μg/ml PMSF. A cell free homogenate (CFH) is formed by dispersing the powdered embryos in the buffer with a tissue homogenizer (Kinematica, Switzerland; model PT10/35) for approximately 30 sec. The homogenate is filtered through three layers of Miracloth (CalBioChem, LaJolla, Calif.) and the filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 100,000×g for one hour to yield a pellet, DP2. The pellet is suspended in 25 mM HEPES and 10% glycerol, at 1/20 of the original CFH volume, to yield the microsomal membrane preparation.

Activity is assayed as described in Example 1. Recovery of acyl-CoA reductase activity is estimated at 30% of the original activity in the cell free homogenate. Acyl-CoA reductase activity in this preparation is stable when stored at −70° C.

B. Solubilization of Reductase Protein

CHAPS (3-[(3-cholamidopropyl)-dimethyl-ammonio]-1-propanesulfonate) and NaCl are added to the microsomal membrane preparation to yield final concentrations of 2% and 0.5M, respectively. The samples are incubated on ice for approximately one hour and then diluted with 25 mM HEPES, 10% glycerol, 0.5M NaCl to lower the CHAPS concentration to 0.75%. The sample is then centrifuged at 240,000×g for one hour and the supernatant recovered and assayed for reductase activity as described in Example 1. Typically, 85% of the reductase activity from the microsomal membrane preparation is recovered in the supernatant fraction. The solubilized reductase activity is stable when stored at −70° C.

C. Blue A Column Chromatography

A column (2.5×8 cm) with a bed volume of approximately 40 ml is prepared which contains Blue A (Cibacron Blue F3GA; Amicon Division, W. R. Grace & Co.), and the column is equilibrated with the following buffer: 0.2M NaCl, 25 mM HEPES, 10% glycerol, 0.75% CHAPS. The solubilized reductase preparation described above is diluted to 0.2M NaCl by addition of a solution consisting of 25 mM HEPES, 10% glycerol, 0.75% CHAPS, and loaded to the Blue A column.

The column is washed with the 0.2M NaCl buffer described above until no protein can be detected (as measured by absorbance at 280 nm) in the buffer flowing through the column. Greater than 90% of the reductase activity binds to the column, while greater than 85% of other protein passes through. Reductase activity is eluted from the column with buffer containing 1.5M NaCl, 25 mM HEPES, 10% glycerol, 0.75% CHAPS. Five ml fractions are collected and assayed for reductase activity as described in Example 1. Fractions containing reductase activity are pooled and stored at −70° C. Typically, 70–80% of the loaded reductase activity is recovered.

D. Size Exclusion Chromatography

A column (2.5×65 cm) is packed with Ultrogel AcA54 medium (Pharmacia LKB Biotechnology, Piscataway, N.J.) equilibrated with buffer containing 0.5M NaCl, 25 mM HEPES, 10% glycerol, 0.75% CHAPS. The column is size calibrated with the following protein standards: bovine serum albumin (66 kD), carbonic anhydrase (29 kD), cytochrome C (12.4 kD), and blue dextran (used to determine the void volume). Four ml of material containing active reductase from the Blue A column is applied to the Ultrogel column which is developed at a linear flow rate of approximately 4.5 cm/hr. Five ml fractions are collected for 8 hr and the reductase activity in the fractions is measured as described in Example 1.

Greater than 40% of loaded activity is recovered in one main peak which elutes at an apparent molecular mass of approximately 49 kD.

E. SDS PAGE Analysis

A 2.5 ml sample of each 5 ml fraction from the Ultrogel column is concentrated using a Centricon 10 microconcentrator device (Amicon Division, W. R. Grace & Co., Danvers, Mass.). The samples are diluted to 200 ul and 100ul of 3× SDS PAGE sample buffer (1×buffer=2% SDS, 30 mM DTT, 0.001% bromphenol blue) is added. An equal volume (100 ul) of each sample is analyzed by electrophoresis on an SDS-polyacrylamide gel, as described by Laemmli (Laemmli, U.K. (1970) *Nature* (London) 227:680–685), except that a 10 to 15% acrylamide gradient is incorporated into the separating portion of the gel. Protein is detected by silver staining (Blum et al., *Electrophoresis* (1987) 8:93–99). Careful examination of the gel reveals only a few polypeptides whose staining intensity in the various fractions can be correlated with the amount of reductase activity detected in those fractions.

One of these is a prominent band which runs just above the 45 kD molecular mass standard (ovalbumin) and is estimated to have an apparent molecular mass of 47 kD. A second, fainter band at approximately 32 kD also correlates with the activity profile.

F. Blotting Proteins to Membranes

Proteins which correlate with acyl-CoA reductase activity may be further isolated for amino acid sequencing by transfer of these proteins to either nitrocellulose or PVDF, either Immobilon-P (Millipore; Bedford, Mass.) or ProBlott (Applied Biosystems; Foster City, Calif.), membranes following SDS-PAGE. Nitrocellulose is preferred when proteins will be subsequently enzymatically digested, while PVDF is useful for N-terminal sequencing methods and for sequencing of peptides resulting from cyanogen bromide digestion.

1. Blotting to Nitrocellulose: When protein is electroblotted to nitrocellulose, the blotting time is 1 hour and the buffer used is 25 mM Tris, 192 mM glycine in 20% methanol. Following electroblotting to nitrocellulose, membranes are stained in 0.1% (w/v) Ponceau S in 1% (v/v) acetic acid for 2 minutes and destained in 2–3 changes of 0.1% (v/v) acetic acid, 2 minutes for each change. Following this, nitrocellulose membranes are stored wet in heat-sealed plastic bage at −20° C. Originally, nitrocellulose membranes were destained in 1% acetic acid and then rinsed with HPLC grade water prior to storage. The stained bands fade rapidly in neutral pH however, so the destain solution was changed to 0.1% acetic acid and membranes were also stored wetted in this solution. If time permits, blots are not frozen but used immediately for digestion to create peptides for determination of amino acid sequence as described below.

2. Blotting to PVDF: When protein is electroblotted to Immobilon P PVDF, the blotting time is 30 minutes and the buffer used in 12.5 mM Tris/5 mM glycine in 10% (v/v) methanol. Following electroblotting to PVDF, membranes are stained in 0.1% (w/v) Coomassie Blue in 50% (v/v) methanol/10% (v/v) acetic acid for 5 minutes and destained in 2-3 changes of 50% (v/v) methanol/10% (v/v) acetic acid, 2 minutes for each change. Following this, PVDF membranes are allowed to air dry for 30 minutes and are then stored dry in heat-sealed plastic bags at $-20°$ C. Protein blotted to PVDF is used directly to determine N-terminal sequence of the intact protein. A protocol for electroblotting proteins to ProBlott is described below in Example 4A.

Example 4

Determination of Amino Acid Sequence

In this Example, methods for determination of amino acid sequences of plant proteins associated with acyl-CoA reductase activity are described.

Cyanogen Bromide Cleavage of Protein and Separation of Peptides

Cyanogen bromide cleavage is performed on the protein of interest using the methodology described in the Probe-Design Peptide Separation System Technical Manual from Promega, Inc. (Madison, Wis.). The 47 kd protein associated with acyl-CoA reductase activity is blotted to an Immobilon-P PVDF membrane as described above. Protein bands are cut out of the blot and each band is placed in a 1.5 ml microcentrifuge tube containing 200 µl of a 10 mg/ml solution of cyanogen bromide in 70% (v/v) formic acid. Protein bands are incubated in this solution overnight at room temperature, and following this incubation the cyanogen bromide solutions are removed and pooled. The pooled solution is dried under a continuous nitrogen stream using a Reacti-Vap Evaporator (Pierce, Rockford, Ill.). Cyanogen bromide peptides are eluted off the Immobilon-P PVDF membrane using a peptide elution solvent with the following composition: 70% (v/v) isopropanol, 0.2% (v/v) trifluoroacetic acid, 0.1 mM lysine, and 0.1 mM thioglycolic acid. 200 µl of this elution solvent is added to each tube and tubes are incubated for 2 hours at room temperature with occasional vortexing. The elution solvents are then removed from each tube, pooled, added to the tube containing the dried cyanogen bromide solution, and dried as described above. The elution procedure is repeated with fresh elution solvent for an additional 2 hours and the pooled solvent is added to the previously dried material and again dried. 50 µl of HPLC grade water is then added to the dried peptides and the water removed by evaporation in a Speed-Vac (Savant, Inc., Farmingdale, N.Y.).

Peptides are separated using a Tris/Tricine SDS-PAGE system similar to that described by Schägger and von Jagow (*Anal. Biochem.* (1987) 166:368-379) may be used. Either 16% or 10-20% (gradient) acrylamide tricine-SDS-PAGE pre-cast gels (Novex Inc., Encinitas, Calif.), are used for the separation. Gels are run in a Tall Mighty Small electrophoresis apparatus from Hoefer Scientific Instruments (San Francisco, Calif.). Prior to electrophoresis of the peptides, gels are pre-run with thioglycolic acid added to the cathode buffer at a concentration of 0.1-0.2 mM for 30-60 minutes at a constant voltage of 30 volts. Running buffer used is made up from a 10× stock, also from Novex; final concentration (1×) is 0.1M Tris, 0.1M Tricine and 0.1% (w/v) SDS. The dried peptides are resuspended in 15µl HPLC grade water and 15 µl 2× sample buffer consisting of: 0.125M Tris-HCl, 2% (w/v) SDS, 5% (v/v) β-mercaptoethanol, 20% (v/v) glycerol, and 0.0025% (w/v) bromphenol blue, and boiled for 5 minutes prior to loading on the gel.

Gels are run at a constant voltage of 125-150 volts for approximately 1 hour or until the tracking dye has begun to run off the bottom edge of the gel. Gels are soaked in transfer buffer (125 mM Tris, 50 mM glycine, 10% (v/v) methanol) for 15-30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3×2 min. in 50% (v/v) methanol/10% (v/v) acetic acid. Membranes are air-dried for 30-45 minutes before storing dry at $-20°$ C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

In this manner, the sequence of a cyanogen bromide fragment of the 47 kD protein is determined, which sequence (SEQ ID NO: 2) is:

Ile Xaa Val Gln Gly Pro Glu Xaa Ile Ala Phe Asp Leu Xaa Xaa
 1           5               10              15 wherein the three-letter abbreviation for amino acids is used and Xaa indicates an unidentified amino acid. It is postulated that the unidentified amino acid at position 2 may be either serine or glutamine, at position 8 it may be serine, at position 14 it may be leucine, and that at position 15 it may be glycine.

B. Protease Digestion and Separation of Peptides

Proteins blotted to nitrocellulose are subjected to digestion with proteases in order to obtain peptides for sequencing. The method used is that of Aebersold, et al. (*PNAS* (1987) 84:6970). Bands of the 47 kD protein, and also an equal amount of blank nitrocellulose to be used as a control, are cut out of the nitrocellulose membrane and washed several times with HPLC grade water in order to remove the Ponceau S. The Ponceau S is not always removable if the blot has been frozen, but the presence of the stain apparently has no effect on the digest procedure. Following this wash, 1.0 ml of 0.5% polyvinylpyrrolidone (PVP-40, Aldrich, Milwaukee, Wis.) in 0.5% acetic acid is added to the membrane pieces and this mixture is incubated for 30 minutes at 37° C. The PVP-40 is needed to block sites on the nitrocellulose which would bind the protease and/or peptides released by the protease digestion.

In order to remove the PVP-40 completely, nitrocellulose pieces are washed with many volumes of HPLC grade water (8×5 ml), checking the absorbance of the washes at 214nm on a spectrophotometer. Also, PVP-40 is more easily removed if bands are not cut into small pieces until after PVP-40 treatment and washing. These two modifications eliminate interference problems with the PVP-40.

Following this extensive washing out of the excess PVP-40, bands are dropped into pieces ~1×2 mm in size. The pieces are then suspended in either trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5-10% (v/v). Proteases, (trypsin or endoproteinase gluC) are diluted in digest buffer and added to the digest mixture in a ratio of 1:10 (w/w) protease to protein. Final volume of the digest mixture is 100 μl. Digests are incubated 18-24 hours. Trypsin digests are incubated at 37° C. and endoproteinase gluC digests are incubated at room temperature. Similarly, other proteases may be used to digest the reductase proteins, including but not limited to lysC and aspN. While the individual digest buffer conditions may be different, the protocols for digestion, peptide separation, purification and sequencing are substantially the same as those described herein for digestion with trypsin and gluC.

Following overnight incubation, digest reactions are stopped by the addition of 10 μl 10% (v/v) trifluoroacetic acid (TFA) or 1 μl 100% TFA. The digest mixture is removed from the nitrocellulose pieces, the nitrocellulose pieces are washed with 1-5 100 μl volumes of digest buffer with 5-10% acetonitrile, and these volumes are concentrated to a volume of less than 100 μl in a Speed-Vac. These concentrates are then injected over a Vydac reverse phase Protein & Peptide C18 column (2.1mm×100mm) installed in an Applied Biosystems (Foster City, Calif.) Model 130 High Performance Liquid Chromatograph (HPLC). Mobile phases used to elute peptides were: Buffer A: 0.1 mM sodium phosphate, pH2.2; Buffer B: 70% acetonitrile in 0.1 mM sodium phosphate, pH2.2. A 3-step gradient of 10-55% buffer B over two hours, 55-75% buffer B over 5 minutes, and 75% buffer B isocratic for 15 minutes at a flow rate of 50 μl/minute is used. Peptides are detected at 214nm, collected by hand, and then stored at −20° C.

C. Reduction and Alkylation of Cysteine Residues

Digested protein can be reduced with β-mercaptoethanol and alkylated with $^3$H-labelled iodoacetic acid as a method to improve identification of cysteine residues when the peptides are sequenced. The β-mercaptoethanol is added to freshly digested protein at a molar ratio of 20:1 over the assumed concentration of sulfhydryl groups in the sample and peptides are incubated at room temperature for 30 minutes. $^3$H-labelled iodoacetic acid is then added at a concentration of 1.1 times the concentration of β-mercaptoethanol and the peptides are incubated in darkness (covered with foil )at room temperature for 60 minutes. To stop the alklylation, more β-mercaptoethanol is added at a concentration of one-tenth of that used to reduce the peptides. Ten μl of 10% TFA is then added as usual to stop any further action of the protease. This can not be added prior to the reduction/alkylation as those reactions work best under the basic pH conditions present in the digest mixture. The reduced/alkylated protein is then concentrated in a Speed-Vac prior to separation of the peptides by HPLC, as described above.

D. N-terminal Sequencing of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5-30 pmoles), the 477A conversion cycle and the 120A analyzer as described by Tempst and Riviere (*Anal. Biochem.* (1989) 183:290).

In this manner, the N-terminal sequence of the 47 kD protein associated with reductase activity is determined, and the sequence (SEQ ID NO: 1) is:

Xaa Xaa Ala Ala Thr Ile Leu Ala Gly Val Xaa Val Leu Val Ala Leu
 1           5                  10                 15

Tyr Asp Gly Leu
  20 wherein the three-letter abbreviation for amino acids is used; Xaa indicates unidentified amino acids. The unidentified amino acid at position 11 is likely a leucine.

Example 5

Jojoba cDNA Library

Construction of jojoba embryo cDNA libraries from poly(A)+RNA isolated from jojoba embryos collected at 80-90 days post-anthesis is described.

A. Jojoba RNA Isolation.

RNA is isolated from polyribosomes by a method initially described by Jackson and Larkins (*Plant Physiol.* (1976) 57:5-10) as modified by Goldberg et al. (*Developmental Biol.* (1981) 83:201-217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM MgCl$_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-lauryl-sarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000×g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5 M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

B. cDNA Library Construction in a Plasmid Vector

Polyadenylated RNA is used to construct a cDNA library in the plasmid cloning vector pCGN1703, derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into *E. coli* strain DH5α (BRL, Gaithersburg, Md.) to generate the cDNA library. The jojoba embryo cDNA bank contains between approximately $1.5 \times 10^6$ clones with an average cDNA insert size of approximately 500 base pairs.

C. cDNA Library Construction in a Lambda Vector

Jojoba polyadenylated RNA is also used to construct a cDNA library in the cloning vector λZAPII/EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations.

The cDNA library constructed in this manner contains approximately $1 \times 10^6$ clones with an average cDNA insert size of approximately 400 base pairs.

The above results demonstrate the ability to obtain solubilized seed-plant fatty acyl reductase protein which is active in the formation of a fatty alcohol. Methods to obtain the acyl reductase protein and amino acid sequences thereof are provided. In addition, methods to obtain reductase nucleic acid sequences from the amino acid sequences are also provided. These nucleic acid sequences may be manipulated to provide for transcription of the sequences and/or expression of reductase proteins in host cells, which proteins may be used for a variety of applications.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

---

---

What is claimed is:

1. A jojoba embryo protein preparation comprising solubilized fatty acyl-CoA reductase wherein said reductase catalyzes the reduction of a fatty acyl substrate to the corresponding alcohol and wherein said reductase has an estimated molecular weight of less than about 90 kD by size exclusion chromatography.

2. The jojoba embryo protein preparation of claim 1 wherein said reductase catalyzes reduction of a fatty acyl-CoA or fatty acyl-ACP substrate to the corresponding alcohol.

3. The jojoba embryo protein preparation of claim 2 wherein the carbon chain of said fatty acyl substrate has the formula $C_{2x}$, wherein X is selected from the group 8-12, and wherein said carbon chain is unsaturated, or is mono-unsaturated.

4. The jojoba embryo protein preparation of claim 1 wherein said reductase is NADPH-dependent.

5. A jojoba embryo protein preparation prepared by a method comprising the steps of:
    isolating microsomal membranes from jojoba embryo tissue,
    incubating said microsomal membranes on ice in 2% CHAPS and 0.5M NaCl for about one hour,
    adding CHAPS and NaCl to said microsomal membranes to provide a solution comprising about 0.75% CHAPS w/v and about 0.5M NaCl,
    centrifuging said solution at about 240,000×g to provide a pellet and supernatant, and
    recovering solubilized reductase protein in said supernatant,
    wherein said preparation contains fatty acyl-CoA reductase which catalyzes the reduction of a fatty acyl substrate to the corresponding alcohol.

6. The jojoba embryo protein preparation of claim 5, wherein said microsomal membranes are obtained by powdering said jojoba embryo tissue and dispersing said tissue in a high salt solution resulting in a cell free homogenate,
    centrifuging said cell free homogenate to produce a pellet, supernatant and fat pad,
    dialyzing said supernatant, and centrifuging said dialyzate to yield a pellet comprising microsomal membranes.

7. The jojoba embryo protein preparation of claim 5, wherein said method comprises the further step of:
    detecting said solubilized reductase protein by dilution of said supernatant to about 0.3% CHAPS w/v and measuring alcohol production from added $^{14}$C labeled acyl-CoA substrate.

8. The jojoba embryo protein preparation of claim 7, wherein said acyl-CoA substrate is tetracosenoyl-CoA.

9. Jojoba embryo fatty acyl-CoA reductase free of an intact jojoba embryo cell wherein said reductase has an estimated molecular weight of less than about 90 kD by size exclusion chromatography, and wherein said reductase catalyzes the reduction of a fatty acyl substrate to the corresponding alcohol.

* * * * *

SEQUENCE LISTING ( 1 ) GENERAL INFORMATION:
    ( i ) APPLICANT: Pollard, Michael R
                      Metz, James G
    ( i i ) TITLE OF INVENTION: Fatty Acyl Reductases
    ( i i i ) NUMBER OF SEQUENCES: 2

( 2 ) INFORMATION FOR SEQ ID NO:1:
    ( i ) SEQUENCE CHARACTERISTICS:
      ( A ) LENGTH: 20 amino acids
      ( B ) TYPE: amino acid
          ( D ) TOPOLOGY: linear
    ( i i ) MOLECULE TYPE: peptide
    ( x i ) SEQUENCE DESCRIPTION: SEQ ID NO:1:

```
Xaa Xaa Ala Ala Thr Ile Leu Ala Gly Val Xaa Val Leu Val Ala Leu
 1               5                   10                  15
Tyr Asp Gly Leu
             20
```

( 2 ) INFORMATION FOR SEQ ID NO:2:
    ( i ) SEQUENCE CHARACTERISTICS:
      ( A ) LENGTH: 15 amino acids
      ( B ) TYPE: amino acid
          ( D ) TOPOLOGY: linear
    ( i i ) MOLECULE TYPE: peptide
    ( x i ) SEQUENCE DESCRIPTION: SEQ ID NO:2:

```
Ile Xaa Val Gln Gly Pro Glu Xaa Ile Ala Phe Asp Leu Xaa Xaa
 1               5                   10                  15
```